(12) United States Patent
Hoffmann et al.

(10) Patent No.: US 7,858,823 B2
(45) Date of Patent: Dec. 28, 2010

(54) PROCESS FOR CYCLOHEXANECARBOXYLIC ACID DERIVATIVES

(75) Inventors: Ursula Hoffmann, Muttenz (CH); Michael Jansen, Bartenheim (FR); Reinhard Reents, Muenchenstein (CH); Helmut Stahr, Loerrach (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 45 days.

(21) Appl. No.: 12/414,695

(22) Filed: Mar. 31, 2009

(65) Prior Publication Data
US 2009/0253927 A1    Oct. 8, 2009

(30) Foreign Application Priority Data
Apr. 4, 2008  (EP) .................... 08154077
Jan. 22, 2009 (EP) .................... 09151070

(51) Int. Cl.
C07C 61/08    (2006.01)
C07C 229/40   (2006.01)
C07C 51/60    (2006.01)
C07C 327/16   (2006.01)
C07C 255/46   (2006.01)
C07C 231/00   (2006.01)

(52) U.S. Cl. .............. 562/400; 562/457; 562/859; 558/257; 558/378; 564/139

(58) Field of Classification Search .............. 558/257, 558/378; 562/400, 859; 564/139
See application file for complete search history.

(56) References Cited

U.S. PATENT DOCUMENTS

| 2,899,458 A | 8/1959 | Wilson |
| 3,320,305 A | 5/1967 | Wiese |
| 4,129,595 A | 12/1978 | Suzuki |
| 6,426,365 B1 | 7/2002 | Shinkai et al. |
| 2003/0092708 A1 | 5/2003 | Shinkai et al. |
| 2007/0100154 A1 | 5/2007 | Hoffmann et al. |
| 2008/0154059 A1 | 6/2008 | Hoffmann et al. |

FOREIGN PATENT DOCUMENTS

| EP | 1 020 439 | 7/2000 |
| WO | WO 98/54124 | 12/1998 |
| WO | WO 2004/056752 A1 | 7/2004 |
| WO | WO 2005/003116 | 1/2005 |
| WO | WO 2007/051714 | 5/2007 |

OTHER PUBLICATIONS

Shinkai et al., J. Med. Chem., 43, pp. 3566-3572 (2000).
Hauser, M., Journal of the American Chemical Society, vol. 105, pp. 5688-5690 (1983) XP002416563.
March, J. Advanced Organic Chemistry Third Ed. (1985) pp. 388-389, XP002488845.
Roth, et al., J. Med. Chem., vol. 35, No. 9, pp. 1609-1617 (1992) XP002437815.
Creger, P.L., J. Am. Chem. Soc., vol. 92, No. 5, pp. 1397-1398 (1970) XP002437816.
Creger, P.L., Ann. Rep. Med. Chem., 12, pp. 278-287 (1977).
Petragnani et al., Synthesis, pp. 521-578 (1982).
Shiner et al., J. Am. Chem. Soc., 103, pp. 436-442 (1981).
Williams et al., J. Org. Chem., 45, pp. 5082-5088 (1980).
Severin et al., Synthesis, 4, pp. 305-307 (1982).
Tavares et al., J. Med. Chem., 47, pp. 50495056 (2004).
Goossen et al., Adv. Synth. Catal., 345, pp. 943-947 (2003).
*Advanced Organic Chemistry*, 338-339 XP002536290, 1978.

*Primary Examiner*—Kamal A Saeed
*Assistant Examiner*—Kristin Bianchi
(74) *Attorney, Agent, or Firm*—George W. Johnston; Dennis P. Tramaloni; Brian C. Remy

(57) ABSTRACT

A process for the preparation of a compound of formula (I):

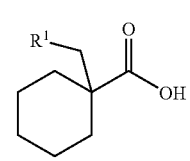

which are useful as intermediates in the preparation of i.a. pharmaceutically active compounds.

20 Claims, No Drawings

PROCESS FOR CYCLOHEXANECARBOXYLIC ACID DERIVATIVES

PRIORITY TO RELATED APPLICATION(S)

This application claims the benefit of European Patent Application No. 08154077.5, filed Apr. 4, 2008, and European Patent Application No. 09151070.1, filed Jan. 22, 2009, which are hereby incorporated by reference in their entirety.

FIELD OF THE INVENTION

The present invention relates generally to a process for the preparation of cyclohexanecarboxylic acid derivatives which are useful as an intermediate in the preparation of pharmaceutically active compounds.

SUMMARY OF THE INVENTION

The present invention generally provides a process for the preparation of a cyclohexanecarboxylic acid derivative of formula (I):

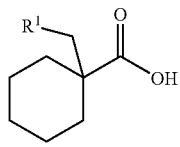

(I)

wherein $R^1$ is $(C_1-C_8)$alkyl, preferably pent-3-yl;

which comprises:

a) hydrolysing a cyclohexanecarbonitrile derivative of formula (II):

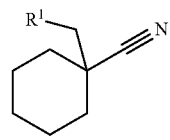

(II)

with $H_2O$ in the presence of a strong acid or with an aqueous base to obtain a cyclohexanecarboxylic acid amide derivative of formula (III):

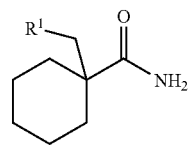

(III)

b) reacting the said cyclohexanecarboxylic acid amide derivative with a nitrosylating agent, to obtain the compound of formula (I).

DETAILED DESCRIPTION OF THE INVENTION

A. Definitions

Unless otherwise stated, the following terms used in the specification and claims have the meanings given below. All references cited herein are hereby incorporated by reference in their entirety.

The term "halo" means fluoro, chloro, bromo or iodo, preferably chloro or bromo.

"Alkali metal" or "alkali" refers to lithium, sodium, potassium, rubidium and caesium. Preferable alkali metal is lithium or sodium. Of these, sodium is most preferred.

"$(C_1-C_8)$alkyl" refers to a branched or straight hydrocarbon chain of one to eight carbon atoms, such as methyl, ethyl, n-propyl, isopropyl, n-butyl, isobutyl, sec-butyl, t-butyl, pentyl, hexyl and heptyl. $(C_1-C_6)$alkyl is preferred.

"$(C_3-C_6)$cycloalkyl" refers to a single saturated carbocyclic ring, such as cyclopropyl, cyclobutyl, cyclopentyl and cyclohexyl.

"$(C_1-C_6)$alkyllithium" is understood as being an $(C_1-C_6)$ alkyl as defined above substituted by a lithium atom, such as butyllithium, hexyllithium, sec-butyllithium.

"Secondary amine" refers to an amine of formula $HNR^2R^3$, wherein $R^2$ and $R^3$ may be the same or different and are independently selected from $(C_1-C_6)$alkyl or $(C_3-C_6)$cycloalkyl, or $R^2$ and $R^3$ taken together with the nitrogen atom to which they are attached, obtain a $(C_4-C_8)$heterocycloalkane optionally containing an additional heteroatom selected from O or N. Representative examples include, but are not limited to, piperidine, 4-methyl-piperidine, piperazine, pyrrolidine, morpholine, dimethylamine, diethylamine, diisopropylamine, dicyclohexylamine, ethylmethylamine, ethylpropylamine and methylpropylamine. Preferably, the secondary amine is chosen from diethylamine, diisopropylamine, dicyclohexylamine, ethylmethylamine, ethylpropylamine, methylpropylamine and morpholine. The more preferred secondary amine is diethylamine or diisopropylamine, most preferred diethylamine. "$(C_4-C_8)$heterocycloalkane" refers to a saturated non-aromatic cyclic compound of 4 to 8 ring atoms in which one or two ring atoms are heteroatoms selected from N or O, and the heterocycloalkane may be optionally substituted with one or more $(C_1-C_3)$alkyl, preferably one $(C_1-C_3)$alkyl.

"Nitrosylating agent" comprises nitrosylsulfuric acid or sodium nitrite or a mixture thereof. Most preferably, the nitrosylating agent is nitrosylsulfuric acid.

"Sulfonate ester of $R^1CH_2$—OH" refers to a substituted or an unsubstituted phenyl-sulfonate, an unsubstituted naphthalene-sulfonate or a $(C_1-C_6)$alkylsulfonate ester derivative of $R^1CH_2$—OH wherein substituted phenyl and the $(C_1-C_6)$ alkyl chain and $R^1$ are as previously defined. Representative examples include, but are not limited to, benzenesulfonic acid 2-ethyl-butyl ester, 1-naphthalenesulfonic acid 2-ethyl-butyl ester, 2-naphthalenesulfonic acid 2-ethyl-butyl ester, toluene-4-sulfonic acid 2-ethyl-butyl ester, 4-nitro-benzenesulfonic acid 2-ethyl-butyl ester, 2,4,6-trimethyl-benzenesulfonic acid 2-ethyl-butyl ester, ethanesulfonic acid 2-ethyl-butyl ester, methanesulfonic acid 2-ethyl-butyl ester and butanesulfonic acid 2-ethyl-butyl ester. "Strong acid" refers to an acid that dissociates completely in an aqueous solution with a $pH \leq 2$. The strong acids include, but are not limited to: sulphuric acid ($H_2SO_4$), hydrohalogenic acid (i.e. HX" wherein X" is I, Br, Cl or F), nitric acid ($HNO_3$), phosphoric acid ($H_3PO_4$) and combinations thereof Preferably, the strong acid is $H_2SO_4$ or hydrohalogenic acid, wherein X" is Br or Cl. Most preferably, the strong acid is $H_2SO_4$. Preferably the concentration of $H_2SO_4$ in water is in the range of 75% to 90%, more preferably 78 to 83%, most preferably 82.5%.

"Aqueous base" refers to a solution comprising a base and water. Numerous bases which readily dissolve in water are known in the art, such as NaOH, KOH, Ca(OH)$_2$, Mg(OH)$_2$, preferably NaOH or KOH. More preferably the aqueous base has a pH of 12 to 14.

B. Detailed Description

In a first aspect, the present invention provides a process for the preparation of a cyclohexanecarboxylic acid derivative of formula (I):

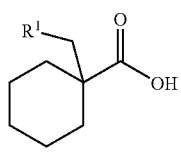

(I)

wherein R$^1$ is (C$_1$-C$_8$)alkyl, preferably pent-3-yl;

which comprises:
a) hydrolysing a cyclohexanecarbonitrile derivative of formula (II):

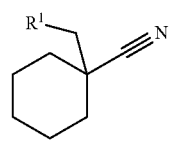

(II)

with H$_2$O in the presence of a strong acid or with an aqueous base to obtain a cyclohexanecarboxylic acid amide derivative of formula (III):

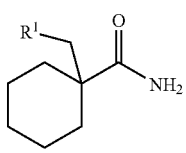

(III)

b) reacting the said cyclohexanecarboxylic acid amide derivative with a nitrosylating agent, to obtain the compound of formula (I).

The compound of formula (I) may be used as an intermediate in the synthesis of valuable pharmaceutical compounds. For example 1-(2-ethyl-butyl)-cyclohexanecarboxylic acid may be used in the synthesis of pharmaceutical compounds as described in EP1,020,439.

Accordingly, in another embodiment the present invention provides a process comprising the synthetic steps represented in the following scheme 1:

Scheme 1:

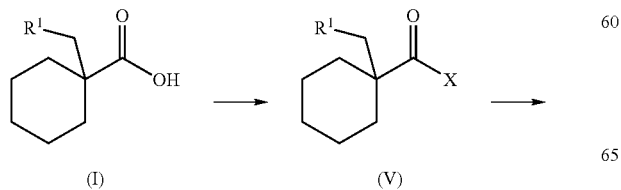

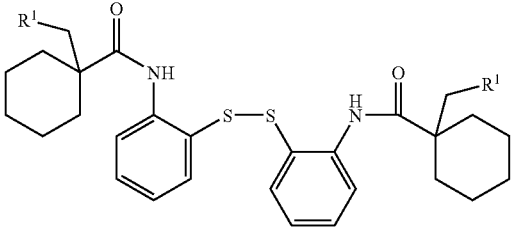

(VI)

↓

(VIII)    (VII)

wherein X is I, Br, Cl or F, R$^1$ is as defined above and R$^4$ is (C$_1$-C$_8$)alkyl. In particular, the process comprises reacting cyclohexanecarboxylic acid derivative of formula (I) with a halogenating agent, such as PX$_3$, PX$_5$, SOX$_2$ or NCX, to obtain the acyl halide of formula (V). The halogenating step is preferably carried out in the presence of tri-(C$_1$-C$_5$)alkylamine. Furthermore, the process comprises reacting the acyl halide with bis(2-aminophenyl)disulfide to acylate the amino groups of the bis(2-aminophenyl)disulfide, reducing the amino-acylated disulfide product with a reducing agent such as triphenylphosphine, zinc or sodium borohydride to yield the thiol product, and acylating the thiol group in the thiol product with R$^4$C(O)X', wherein X' is I, Br, Cl or F.

The additional steps may be performed, e.g., according to the procedures described in Shinkai et al., J. Med. Chem. 43:3566-3572 (2000) or WO 2007/051714, which are hereby incorporated reference.

Preferably the halogenating agent is chosen from thionyl chloride, phosphorus pentachloride, phosphorus tribromide and cyanuric fluoride, oxalylchloride, Cl-trimethylpropenylamine most preferably thionyl chloride. The acyl halide of formula (III) wherein X is Cl is most preferred.

In the thiol acylation step, preferably the acylating agent is R$^4$C(O)X', wherein X' is Cl. Most preferably R$^4$ is isopropyl.

In another embodiment, the present invention provides a process for the preparation of a cyclohexanecarbonitrile derivative of formula (II):

(II)

wherein R$^1$ is as defined above;

which comprises reacting cyclohexanecarbonitrile of formula (IV)

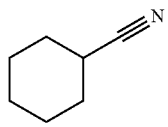
(IV)

with an alkylating agent such as a 1-halo-CH$_2$R$^1$, preferably 1-halo-2-ethylbutane, or a sulfonate ester of R$^1$CH$_2$—OH, preferably of 2-ethyl-1-butanol, in the presence of a secondary amine and (C$_1$-C$_6$)alkyllithium, (C$_3$-C$_6$)cycloalkyllithium or phenyllithium.

Preferably, (C$_1$-C$_6$)alkyllithium, (C$_3$-C$_6$)cycloalkyllithium or phenyllithium with a secondary amine is added to the cyclohexanecarbonitrile of formula (IV), followed by the addition of an alkylating agent.

Preferably the above mentioned coupling reaction is followed by a mineral acid quenching, such as hydrofluoric acid, hydrochloric acid, boric acid, nitric acid, phosphoric acid, acetic acid, formic acid or sulfuric acid, most preferably by hydrochloric acid.

A compound of formula (III), wherein R$^1$ is pent-3-yl, is new. Accordingly, a further embodiment the present invention provides a compound of formula (III')

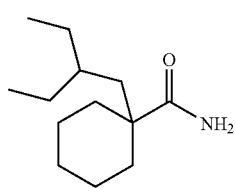
(III')

In yet another embodiment, the present invention provides a process for the preparation of a cyclohexanecarboxylic acid derivative of formula (I):

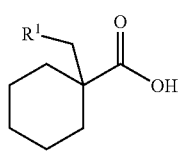
(I)

wherein R$^1$ is as defined above;

which comprises:

a) hydrolysing a cyclohexanecarbonitrile derivative of formula (II):

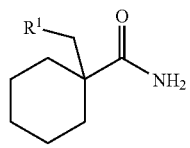
(II)

with H$_2$O in the presence of a strong acid or with an aqueous base to obtain a cyclohexanecarboxylic acid amide derivative of formula (III);

(III)

b) reacting the said cyclohexanecarboxylic acid amide derivative (III) with a nitrosylating agent, to obtain the compound of formula (I);

c) solution extracting the compound of formula (I) preferably out of an organic solvent by adjusting the solution to a basic pH, preferably of pH of 9 to 14, more preferably to pH of 11 to 13.5, most preferably to pH of 12.5 to 13, by addition of a basic aqueous solution, then separate phases, discarding the organic phase, adding fresh organic phase, adjusting the aqueous phase to a pH of 1 to 10, preferably to a pH of 3 to 8, most preferably to a pH of 6 to 7, by acidifying the solution, preferably by addition of a mineral acid, such as hydrofluoric acid, hydrochloric acid, boric acid, nitric acid, phosphoric acid, acetic acid, formic acid or sulfuric acid, most preferably hydrochloric acid and thereby extracting the compound of formula (I) into the organic phase.

Preferably after the hydrolysis of compound (II), steps a) and b), the biphasic mixture is separated, the water solution is back extracted with an organic solvent, and H$_2$O is added to the combined organic phases of the reaction mixture. Then, the pH of the biphasic solution is adjusted to 10 to 14, preferably to a pH of 11 to 13.5 by addition of a basic aqueous solution as defined herein, preferably over a period of 10 min. The organic phase is discarded and a saturated solution of NaCl and an organic solvent, as defined herein, more preferably toluene, is added to the water phase, more preferably the organic phase is discarded and water and an organic solvent is added to the water phase. After this, the pH of the mixture is adjusted to a pH of 6 to 7 by addition of a mineral acid as previously defined. The water phase is discarded and the organic layer is concentrated.

In a further embodiment, the present invention provides a process for the preparation of the compound of formula (I), which comprises the preparation of a cyclohexanecarbonitrile derivative of formula (II) followed by the hydrolysis steps as described above and following scheme 2, wherein R$^1$ is as defined above.

Scheme 2:

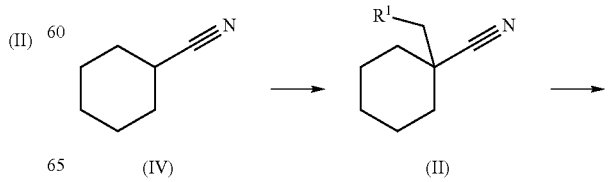
(IV)　　　(II)

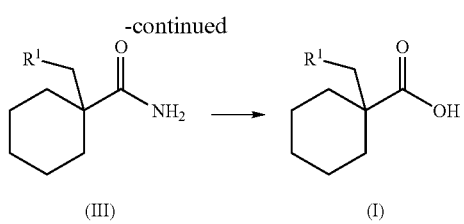

Unless otherwise stated, organic solvent referred herein comprises ether like solvent (e.g. tetrahydrofuran, diisopropyl ether, t-butylmethyl ether or dibutyl ether), an aliphatic hydrocarbon solvent (e.g. hexane, heptane or pentane), a saturated alicyclic hydrocarbon solvent (e.g. cyclohexane or cyclopentane) or aromatic solvent (e.g. toluene or t-butylbenzene).

A nonprotic organic solvent is the preferred solvent during the alkylation, such as tetrahydrofuran, alone or in combination with another nonprotic solvent, e.g. from the group of the apolar solvents hexane, heptane and t-butyl-benzene. Most preferably the nonprotic solvent is tetrahydrofuran.

The preferred lithium agent is $(C_1-C_6)$alkyllithium, and butyllithium is the most preferred.

The preferred alkylating agent is 1-halo-2-ethylbutane, most preferably 1-bromo-2-ethylbutane.

The alkylation is performed preferably under an inert gas atmosphere i.e. under argon or nitrogen.

In a further embodiment, the present invention provides processes as described above wherein nitrosylating agent is generated in situ e.g. mixing $H_2SO_4$ and nitrous acid ($NHO_2$).

Preferably the hydrolysing agent of the cyclohexanecarbonitrile derivative of formula (II) is a strong acid. The most preferred strong acid for step a) is $H_2SO_4$. The hydrolysis step is either carried out by dosing compound of formula (II) to $H_2SO_4$ at temperature of 80° C. to 120° C. or both compound of formula (II) and $H_2SO_4$ are heated as a mixture to a temperature of 80° C. to 120° C. More preferably the temperature in both modes of addition is 95 to 110° C., most preferably 105 to 110° C. 1.5 to 4 equivalents of $H_2SO_4$ with respect to compound of formula (II) is preferably used. More preferably 1.9 to 3.6 equivalents are used. Most preferably 2 equivalents are used. The hydrolysis is carried out with excess $H_2O$, preferably 5 to 25 eq. of $H_2O$ with respect to the compound of formula (II), more preferably 10 to 20 eq. Most preferably, 14 to 16 eq. of $H_2O$ is used with respect to the compound of formula (II).

For the hydrolysis of the amide of formula (III), preferably 1.1-1.4 equivalents of nitrosylsulfuric acid is used, most preferably 1.2 to 1.4 equivalent. Either nitrosylsulfuric acid is firstly added and followed by $H_2O$ or the $H_2O$ is added first then followed by addition of nitrosylsulfuric acid. The second addition mode is preferred. Preferably, the dosing temperature is at 20 to 65° C., most preferably 60 to 65° C.

According to the present invention the "basic aqueous solution" for the extraction step (c) is preferably chosen from inorganic bases or organic bases, a mixture thereof, or from commonly known buffering solutions of suitable pH. The preferred inorganic base is an alkali base, such as alkalicarbonate, alkalibicarbonate, alkali-borate, alkali phosphate, alkali-hydroxide. A more preferred "basic aqueous solution" is chosen from solution of potassium bicarbonate, sodium bicarbonate, potassium carbonate, sodium carbonate, sodium borate, sodium hydroxide, or a mixture thereof. The most preferred "basic aqueous solution" is a solution of sodium bicarbonate, sodium hydroxide or a mixture thereof.

In a further embodiment the present invention provides a process for the preparation of S-[2-([[1-(2-ethylbutyl)-cyclohexyl]-carbonyl]amino)phenyl]2-methylpropanethioate comprising the formation of a compound of formula (II) obtained by any of the processes and conditions mentioned previously.

The methods of the present invention may be carried out as semi-continuous or continuous processes, more preferably as continuous processes. In particular, the process for the preparation of a cyclohexanecarbonitrile derivative of formula (II) may be carried out as semi-continuous or continuous process.

In the case of a continuous conduct of the process for the preparation of a cyclohexanecarbonitrile derivative of formula (II), a solution ($S^1$) of a secondary amine and ($C_1-C_6$) alkyllithium, ($C_3-C_6$)cycloalkyllithium or phenyllithium (most preferably Lithiumdiisopropylamide), and a solution ($S^2$) of a cyclohexanecarbonitrile are continuously added into a reaction vessel while preferably being mixed. Then the mixture from the deprotonation and a solution ($S^3$) of an alkylating agent (most preferably 2-ethylbutylbromide) were added continuously to a second reaction vessel while preferably being mixed. Preferably, the reaction mixture is then treated with HCl, the collected organic phase are washed with water, and concentrated under reduced pressure to yield cyclohexanecarbonitrile derivative of formula (II). In the continuous process, the preferred reaction vessels are microreactors consisting of mixing and reaction chambers.

Preferably the speeds of addition of solution ($S^1$) and solution ($S^2$) are between 1.2-2.1 mmol/min (most preferably 1.64 mmol/min) and between 0.8 and 1.7 mmol/min (most preferably 1.17 mmol/min), respectively. Preferably the contacting time of solution ($S^1$) and ($S^2$) is less than 60 seconds (more preferably less than 30 sec, most preferably 11 sec). Preferably the speeds of addition of solution $S^3$ is 1.29 mmol/min (range 0.9-1.7 mmol/min) and preferably the contacting time is less than 20 min, more preferably is 6 min.

The starting materials and reagents, which do not have their synthetic route explicitly disclosed herein, are generally available from commercial sources or are readily prepared using methods well known to the person skilled in the art. For instance, the compound of formula (IV) is commercially available or can be prepared by procedures known to the skilled person.

EXAMPLES

The following examples are provided for the purpose of further illustration and are not intended to limit the scope of the claimed invention.

The following abbreviations and definitions are used: br (broad); BuLi (butyllithium); CDCl₃ (deuterated chloroform); eq. (equivalent); g (gram); GC (gas chromatography); h (hour); HCl (hydrochloric acid); H₂O (water); HPLC (High-Performance Liquid Chromatography); ISP (Isotopic Spin Population); KOH (Potassium Hydroxide); LDA (Lithium Diisopropylamide); M (Molar); m (multiplet); MS (Mass Spectroscopy); mL (milliliter); NaOH (Sodium hydroxide); NMR (nuclear magnetic resonance); RT (room temperature); s (singlet); t (triplet); THF (tetrahydrofuran);

Example 1

1-(2-Ethyl-butyl)-cyclohexanecarboxylic acid 1.1 1-(2-Ethyl-butyl)-cyclohexylcarbonitrile 26.25 g (259.4 mmol) diisopropylamine were diluted with 24.0 ml anhydrous THF and cooled down to an internal temperature of −15 °C. 73.02 g (263.8 mmol) butyllithium in hexane (2.5 mol/l) were added at a rate that the internal temperature was kept below −2° C. (time of dosage 25 minutes). After completed dosage, the solution was cooled down to −5° C. 24.0 g (219.8 mmol) cyclohexylcarbonitrile were dissolved with 48.0 ml THF and cooled down to 2° C. The prepared LDA-solution (−5° C.) was added within 20 minutes at a rate that the internal temperature was kept below 8.0° C. The lines were rinsed with 6.0 ml THF. The mixture was cooled down to 3.0° C. and treated with 38.1 g (230.8 mmol) 2-ethylbutylbromide dissolved in 30.0 ml THF within 15 minutes, allowing the internal temperature to reach 26° C. The lines were rinsed with 6.0 ml THF and the yellow solution was stirred at room temperature. 120 ml water was added and a pH-value of 1 was adjusted by adding 35.0 ml HCl conc. The biphasic mixture was extracted three times with hexane (total 264 ml) and the collected hexane phases were washed with water. The organic phase was dried over sodium sulfate and concentrated under reduced pressure at 53° C. to afford 43.75 g of 1-(2-ethyl-butyl)-cyclohexylcarbonitrile_ as a clear yellowish slightly oily residue (HPLC assay 95.3 area %, 103.0% yield, not corrected).

$H^1$ NMR (400 MHZ, $CDCl_3$, ppm). 0.87 (t, 6H), 1.18-1.25 (m, 3H), 1.38-1.44 (m, 7H), 1.62-1.72 (m, 5H), 1.97 (d, 2H).

MS (ISP): 194 ([M+H$^+$] 4), 164 (57), 138 (100), 109 (47).

1.2 1-(2-Ethyl-butyl)-cyclohexanecarboxylic acid 10.0 g (51.7 mmol) 1-(2-ethyl-butyl)-cyclohexylcarbonitrile were heated in 21.8 g (183.7 mmol) $H_2SO_4$ (82.5% solution in water) at 100° C. for 4 hours. The reaction mixture was cooled down to room temperature and dosed with 23.0 g (72.4 mmol) nitrosylsulfuric acid. To the reaction mixture 25.0 ml of $H_2O$ was added within 1 hour, allowing the internal temperature to reach 40° C. (cooling, exothermic reaction). After completed dosage, 25.0 ml $H_2O$ were added additionally. After the addition of 30.0 g hexane the phases were separated and the aqueous phase was extracted twice with hexane (total 80.0 g). The collected organic phases were washed with 24.0 ml $H_2O$ and dried over sodium sulfate. Evaporation of the organic phase under reduced pressure gave 10.12 g of 1-(2-ethyl-butyl)-cyclohexanecarboxylic acid as slightly viscous yellowish oil which crystallized after the addition of seed crystals (HPLC assay 95.2% m/m, yield 88%).

$H^1$ NMR (400 MHZ, $CDCl_3$, ppm). 0.81 (t, 6H), 1.20-1.38 (m, 10H), 1.47 (d, 2H), 1.58-1.61 (m, 3H), 2.085 (d, 2H), 11.4 (s, —COOH).

MS (ISP): 211 [M−H]

Example 2

1-(2-Ethyl-butyl)-cyclohexanecarboxylic acid amide 21.3 g (110.2 mmol) 1-(2-ethyl-butyl)cyclohexylcarbonitrile and 46.5 g (391.2 mmol) $H_2SO_4$ (82.5% solution in water) were mixed, heated to 100° C. and stirred for 3 h at 100° C. After that time, the reaction mixture was cooled down to 20° C., quenched with 50.0 mL water and the pH was adjusted to pH=7-8 by addition of 86.0 mL of NaOH 28%. 50 mL of methylenechloride was added and after phase separation, the aqueous phase was extracted again with 50.0 ml methylenechloride. The organic phases were combined and concentrated in vacuo. The residue was crystallized from n-hexanes. 16.5 g of 1-(2-ethyl-butyl)-cyclohexanecarboxylic acid amide were obtained as colorless crystals with an HPLC assay of 100.0% m/m (yield 70.8%).

IR; 3426, 2923, 2855, 1632, 1459, 1379, 511 cm-1

$H^1$NMR (400 MHz, $CDCl_3$, ppm): 5.63 (br.s., 2H), 1.93 (m, 2H), 1.64-1.53 (m, 3H), 1.49-1.38 (m, 4H), 1.36-1.22 (m, 8H), 0.81 (t, 6H)

MS(ISP): 212 (M+1)$^+$

Anal. Calc. for $C_{13}H_{25}NO$: C, 73.88; H, 11.92; N, 6.63. Found: C, 73.77; H, 11.66; N, 6.61

Example 3

1-(2-Ethyl-butyl)-cyclohexanecarboxylic acid 1-(2-Ethyl-butyl)cyclohexylcarbonitrile 10.0 g (51.7 mmol) and $H_2SO_4$ (75.0% solution in water) 20 g (153 mmol) were mixed, heated to 105° C. and stirred for 10 h at 105° C. No starting material remained by GC analysis. After that time, the reaction mixture was cooled down to 15° C. Sodium nitrite 4.28 g (62.0 mmol) were added in portions giving rise to vigorous reaction with considerable gas evolution. Further portions of sodium nitrite were added resulting in a total of 5.34 g (77.4 mmol). Water (20 ml) and toluene (30 ml) were added to the reaction mixture and the two clear layers were separated. The lower aqueous layer was washed with toluene (15 ml) and the toluene layers combined. The combined toluene layers were washed with aqueous sodium hydrogen carbonate (15 ml) buffered to pH 9 followed by a further two aqueous sodium bicarbonate washes (10 ml each). The combined toluene layers were concentrated in vacuo giving 1-(2-ethyl-butyl)-cyclohexanecarboxylic acid (I), 8.45 g with a GC assay of 93% m/m (yield 77%).

Example 4

1-(2-Ethyl-butyl)-cyclohexanecarboxylic acid

To a continuously stirred solution of 23.8 g (200 mmol) of $H_2SO_4$ (82.5% solution in water) heated to 105° C.-110° C., was added dropwise, over a period of 60 min, under argon, 20.4 g (100 mmol) of 1-(2-Ethyl-butyl)cyclohexylcarbonitrile. Then, the reaction mixture was stirred for a further 2 h at 105° C.-110° C. No starting material remained by GC analysis (less than 0.5% of starting nitrile remained in the mixture). Once the reaction mixture was cooled down to 65° C., 100 ml of hexane was added. Then, 26.5 g (1.47 mol) of $H_2O$ was added over a period 5 to 10 min. To the two phases reaction mixture, at 60-65° C., under heavy stirring (800 rpm), over a period of 60 min, was added 44.5 g (140 mmol) of nitrosylsulfuric acid (40% in sulfuric acid), with the help of an infusion pump. The reaction mixture was stirred for a further 30 min at 60-65° C. The reaction mixture was allowed to cool and settle down to room temperature. The aqueous phase was discarded. Then to the organic phase was added 100.0 ml $H_2O$. The pH of the solution was adjusted to 12.5-13 by addition of approximately 38 g of sodium hydroxide (28% solution in water) at 20-30° C. while stirring, over a 10 min period with the help of dropping funnel. Both phases were allowed to separate for 5 min. The organic phase was discarded and 24 g (20 ml) saturated solution of NaCl and 240 ml of toluene were added to the water phase. Over a 10 min period, with the help of dropping funnel, while stirring the pH was adjusted to 6-7 with approximately 26 g HCl ( 37% solution in water). Both phases were allowed to separate for 5 min. The organic layer was concentrated under reduced pressure at giving 1-(2-ethyl-butyl)-cyclohexanecarboxylic acid, 20.6 g with a GC assay of 98.1% m/m (yield 95%).

Example 5

1-(2-Ethyl-butyl)-cyclohexanecarboxylic acid

To a continuously stirred solution of 23.8 g (200 mmol) of $H_2SO_4$ (82.5% solution in water) heated to 105° C.-110° C., was added dropwise, over a period of 60 min, under argon, 20.9 g (100 mmol) of 1-(2-Ethyl-butyl)cyclohexylcarbonitrile. Then, the reaction mixture was stirred for a further 2 h at 105° C.-110° C. No starting material remained by GC analysis (less than 0.5% of starting nitrile remained in the mixture). Once the reaction mixture was cooled down to 65° C., 100 ml of heptane was added. Then, 26.5 g (1.47 mol) of $H_2O$ was added over a period 5 to 10 min. To the two phases reaction mixture, at 60-65° C., under heavy stirring (800 rpm), over a period of 60 min, was added 47.7 g (140 mmol) of nitrosylsulfuric acid (40% in sulfuric acid), with the help of an infusion pump. The reaction mixture was stirred for a further 30 min at 60-65° C. The reaction mixture was allowed to cool and settle down to room temperature. The aqueous phase was discarded. Then to the organic phase was added 100.0 ml $H_2O$. The pH of the solution was adjusted to 12.5-13 by addition of approximately 17 g of sodium hydroxide (28% solution in water) at 20-30° C. while stirring, over a 10 min period with the help of dropping funnel. Both phases were allowed to separate for 5 min. The organic phase was discarded and 240 ml of toluene were added to the water phase. Over a 10 min period, with the help of dropping funnel, while stirring the pH was adjusted to 6-7 with approximately 12 g HCl (37% solution in water). Both phases were allowed to separate for 5 min. The organic layer was concentrated under reduced pressure at giving 1-(2-ethyl-butyl)-cyclohexanecarboxylic acid in toluene, 37.0 g with a GC assay of 52.1% m/m (yield 90.7%).

Example 6

1-(2-Ethyl-butyl)-cyclohexylcarbonitrile

EHRFELD's microreactor units were used in the following example.

Preparation of Solutions:
  111 ml (200 mmol) Lithiumdiisopropylamide (LDA) solution in THF are diluted with 55 ml THF
  15.4 g (141 mmol) Cyclohexylcarbonitrile are dissolved in 200 ml of solvent mixture (33% THF, 50% Heptane, 17.4% Ethylbenzene)
  25.8 g (156 mmol) 2-Ethylbutylbromide are dissolved in 200 ml of solvent mixture (33% THF, 50% Heptane, 17.4% Ethylbenzene)
  Conditioning of Microreaction—System with small flux THF Reaction:
  Above LDA-solution is dosed with a flow of 1.36 ml/min (1.64 mmol/min) into a mixing device. A second flow of cyclohexylcarbonitrile with 1.8 ml/min (1.17 mmol/min) is dosed into the same mixer at 25° C.
  After a residence time of 11 sec. an ethylbutyl bromide flux with 1.83 ml/min (1.29 mmol/min) meets the flux from the first mixer in a second mixing device. The residence time until entering the heated micro reactor is 6 sec. at 25° C.
  Residence time in the micro reactor is about 360 sec. Flux temperature at reactor outlet is 58° C. The reaction mixture is cooled and dosed into a container with 70 ml HCl 1N (140 mmol). This mixture is stirred for 30 min and extracted with n-heptane.

The organic phase is evaporated first at 50° C. at 150 mbar, then at 80° C. and 15 mbar. 31.4 g (162 mmol, assay: 78.7%, yield: 91%) 1-(2-ethyl-butyl)-cyclohexylcarbonitrile are obtained.

The invention claimed is:

1. A process for the preparation of a cyclohexanecarboxylic acid derivative of formula (I):

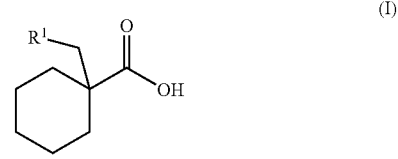

wherein $R^1$ is a $(C_1-C_8)$alkyl,
which comprises the following steps:
  a) hydrolysing a cyclohexanecarbonitrile derivative of formula (II):

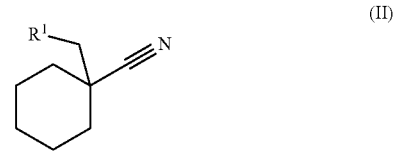

with $H_2O$ in the presence of a strong acid, or with an aqueous base, to obtain a cyclohexanecarboxylic acid amide derivative of formula (III);

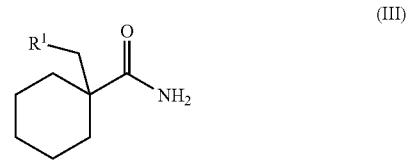

b) reacting the said cyclohexanecarboxylic acid amide derivative with a nitrosylating agent, to obtain the compound of formula (I).

2. The process of claim 1, wherein the cyclohexanecarbonitrile derivative of formula (II) is prepared by reacting a cyclohexanecarbonitrile of formula (IV)

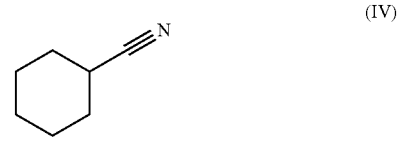

with an alkylating agent in the presence of a secondary amine and $(C_1-C_6)$alkyllithium, $(C_3-C_6)$cycloalkyllithium or phenyllithium to obtain a compound for formula (II).

3. The process of claim 2, wherein the secondary amine is diisopropylamine.

4. The process of claim 2, wherein the $(C_1-C_6)$alkyllithium is butyllithium.

5. The process of claim 1, further comprising solution extracting the compound of formula (I) by adjusting the solution to a basic pH, then adjusting the aqueous phase to a pH of 1-10 by addition of a mineral acid.

6. The process of claim 1, additionally comprising the step of reacting a halogenating agent in the presence of a tri-($C_1$-$C_5$)alkylamine with a compound of formula (I), to yield a compound of formula (V), wherein X is I, Br, Cl or F:

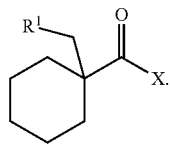
(V)

7. The process of claim 6 which further comprises the step of acylating a compound of formula (VI'):

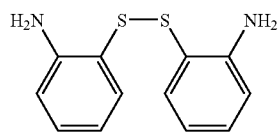
(VI')

with a compound of formula (V) to yield a compound of formula (VI):

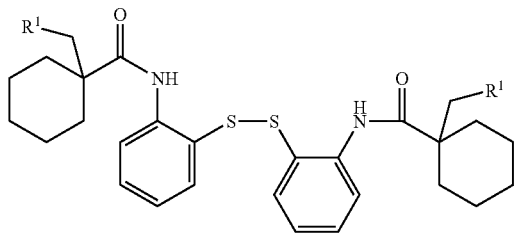
(VI)

wherein $R^1$ is a ($C_1$-$C_8$)alkyl.

8. The process of claim 7 which further comprises the step of reducing the compound of formula (VI) with a reducing agent to yield a compound of formula (VII), wherein $R^1$ is a ($C_1$-$C_8$)alkyl:

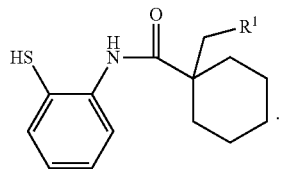
(VII)

9. The process of claim 8 which further comprises the step of acylating the compound of formula (VII) with $R^4C(O)X'$, wherein $X'$ is I, Br, Cl or F, to yield a compound of formula (VIII):

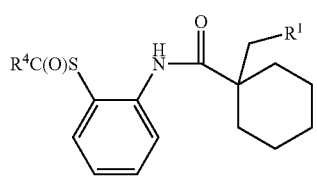
(VIII)

wherein $R^4$ is $C_1$-$C_8$alkyl and $R^1$ is a ($C_1$-$C_8$)alkyl.

10. The process of claim 2, wherein the alkylating agent is 1-bromo-2-ethylbutane.

11. The process of claim 1, wherein the nitrosylating agent is generated in situ.

12. The process of claim 9 wherein the compound of formula (VIII) is S-[2-([[1-(2-ethylbutyl)-cyclohexyl]-carbonyl]amino)phenyl]2-methylpropanethioate.

13. The process of claim 1, wherein the process is semi-continuous or continuous.

14. The process of claim 1, wherein $R^1$ is pent-3-yl.

15. The process of claim 1, wherein the strong acid in step (a) is sulphuric acid.

16. The process of claim 1, wherein the strong acid in step (a) is hydrohalogenic acid.

17. The process of claim 1, wherein the aqueous base in step (a) is NaOH or KOH.

18. The process of claim 2, wherein the alkylating agent is 1-halo-$CH_2R^1$.

19. The process of claim 2, wherein the alkylating agent is a sulfonate ester of $R^1CH_2$—OH.

20. The process of claim 5, wherein the mineral acid is HCl.

* * * * *